United States Patent [19]

Hegasy et al.

[11] Patent Number: 5,264,446
[45] Date of Patent: Nov. 23, 1993

[54] SOLID MEDICAMENT FORMULATIONS CONTAINING NIFEDIPINE, AND PROCESSES FOR THEIR PREPARATION

[75] Inventors: Ahmed Hegasy, Leverkusen, Fed. Rep. of Germany; Klaus-Dieter Ramsch, Heerlen, Netherlands

[73] Assignee: Bayer Aktiengesellschaft, Leverkusen, Fed. Rep. of Germany

[21] Appl. No.: 892,439

[22] Filed: Jun. 1, 1992

Related U.S. Application Data

[63] Continuation of Ser. No. 576,103, Aug. 29, 1990, abandoned, which is a continuation of Ser. No. 403,417, Sep. 1, 1989, abandoned, which is a continuation of Ser. No. 745,339, Jun. 14, 1985, abandoned, which is a continuation of Ser. No. 478,216, Mar. 24, 1983, abandoned, which is a continuation of Ser. No. 294,608, Aug. 20, 1981, abandoned.

[30] Foreign Application Priority Data

Sep. 9, 1980 [DE] Fed. Rep. of Germany ....... 3033919

[51] Int. Cl.$^5$ .................... C07D 213/55; A61K 31/44
[52] U.S. Cl. ...................................... 514/356; 546/321
[58] Field of Search .......................... 546/321; 514/356

[56] References Cited

U.S. PATENT DOCUMENTS

| | | | |
|---|---|---|---|
| 3,330,727 | 7/1967 | Lees | 514/462 |
| 3,485,847 | 12/1969 | Bossert et al. | 546/321 |
| 3,784,684 | 1/1974 | Bossert et al. | 514/356 |

FOREIGN PATENT DOCUMENTS

| | | | |
|---|---|---|---|
| 0047899 | 8/1981 | European Pat. Off. | 514/356 |
| 1456618 | 11/1976 | United Kingdom | 514/356 |

OTHER PUBLICATIONS

W. A. Ritschel, "In Vivo Animal Models for Bioavailablity Assessment", S. T. P. Pharama 3(2) 125–141, 1987.
Levy et al, "Development of In Vitro Dissolution Tests which . . . ", J. of Pharm. Sciences, vol. 54, No. 12 (1965) 1719–1722.
B. Katchen, "Correlation of Dissolution Rate and . . . ", J. of Pharm. Sciences, vol. 56, No. 9 (1967), 1108–1111.
"Benoxaprofen, A New Anti-Inflammatory Agent: Particle-Size Effect on Dissolution Rate and Oral Absorption in Humans", A. Ridolfo, L. Thompkins, L. D. Bechtol and R. H. Carmichael, *Journal of Pharmaceutical Sciences, vol. 68, No. 7, Jul. 1979.*
Von H. Schwela, et al, *Medicamentum, Berlin, 19 258–261 (1978).*
Sugimoto, Drug Development and Industrial Pharmacy, vol. 6, No. 2 (1980), pp. 137–151.
Patzschke et al, 2nd International "ADALAT" Symposium, edited by Wilhelm-Lochner-Wolfgang Braasch, pp. 27–32, (1975).
Journal of Phamaceutical Sciences, Nov. 1968, vol. 57, No. 11, "Particle Size of Drugs And Its Relationship To Absorption And Activity", Julian H. Fincher, pp. 1825–1835.
Drug Development and Industrial Pharmacy, vol. 6, No. 2, 1980, pp. 137–160.
Nature, Feb. 10, 1962, vol. 193, pp. 588–589, Atkinson et al, "Effect of Particle Size on Blood Griseofulvin-Levels in Man".

*Primary Examiner*—Alan L. Rotman
*Attorney, Agent, or Firm*—Sprung Horn Kramer & Woods

[57] ABSTRACT

The invention is directed to the provision of solid pharmaceutical compositions (and methods for their preparation) containing nifidipine crystals with a specific surface area of 1.0 to 4.0 m$^2$/g., in admixture with a solid diluent. The said compositions overcome the deficiencies of prior art compositions containing nifidipine, which is known to have effect as a coronary vasodilator.

12 Claims, No Drawings

SOLID MEDICAMENT FORMULATIONS CONTAINING NIFEDIPINE, AND PROCESSES FOR THEIR PREPARATION

This application is a continuation of application Ser. No. 576,103, filed Aug. 29, 1990, abandoned, which is a continuation of Ser. No. 403,417, filed Sep. 1, 1989, now abandoned, which is a continuation of Ser. No. 745,339, filed Jun. 14, 1985, now abandoned, which is a continuation of Ser. No. 478,216, filed Mar. 24, 1983, now abandoned, which is a continuation of Ser. No. 294,608 filed Jun. 20, 1981, now abandoned.

The present invention relates to novel particular solid medicament formulations containing the known compound nifedipine, which has an action on the circulation (e.g. coronary vasodilators), and to process for their production.

It has already been disclosed that the compound nifedipine has very powerful actions which influence the circulation (see British Patent Specification 1,173,862). Because nifedipine is sensitive to light and sparingly soluble, a number of difficulties occur in the galenical formulation of medicamental specialities, as is seen from numerous patents and patent applications for special formulations of this active compound. Thus, for example, U.S. Pat. No. 3,784,684 relates to particular gelatin capsules for chewing which certain nifedipine and as a result of which the coronary action of nifedipine can be advantageously utilised. Furthermore, British Patent Specification 1,456,618 describes and claims solid medicament formulations which likewise ensure a good bio-availability of nifedipine. Solid medicament forms in which the poor solubility of nifedipine is said to be compensated by using certain solubilizing agents and surface-active substances are also described in DT-OS (German Published Specification) 2,822,882. The ease of absorption of nifedipine as a result of using polyethylene glycol and certain porous excipient substances is also said to be improved in European Published Patent Application 1,247.

All previous attempts to compensate the poor solubility of nifedipine by certain measures and at the same time to ensure good bio-availability have a number of disadvantages. The use of surface-active substances, solubilising agents and certain excipient substances which have a particular surface, for example are porous, frequently leads to administration forms in which the preparations are undesirably large in size. In order to facilitate swallowing, such tablets or capsules are frequently converted into particular shapes, such as, ellipsoids or elongate shapes, but this no longer leads to satisfactory results in the case of preparations weighing over 400 mg. More frequent intake of smaller preparations also does not provide a satisfactory solution.

For medicament formulations, both the number and the amount of auxiliaries and excipients should be kept as low as possible. On comparison of two medicament specialties, that preparation which, in addition to the active compound, contains as few auxiliaries and additives as possible is always preferred, in order largely to avoid undesired biological actions.

A further disadvantages of the nifedipine-containing preparations which have been known hitherto is the expensive process for producing them, this disadvantage applying, in particular, to liquid formulations and capsule preparations. The high sensitivity of nifedipine to light and its poor solubility result in expensive process measures which, especially in the case of liquid formulations, require, as protection from light, exclusion of daylight and the use of sodium light.

According to the present invention there are provided solid pharmaceutical compositions containing as the active ingredient nifedipine crystals with a specific surface area of 0.5 to 6 $m^2g$, in admixture with a solid diluent.

The invention also provides a solid medicament in dosage unit form comprising nifedipine crystals with a specific surface area of 0.5 to 6 $m^2g$.

The invention also provides medicament in the form of tablets (including lozenges and granules), dragees, capsules, pills, suppositories, sachet or multiphase preparations, such as two-layer tablets comprising nifedipine crystals with a specific surface area of 0.5 to 6 $m^2/g$.

"Medicament" as used in this Specification means physically discrete coherent portions suitable for medical administration. "Medicament in dosage unit form" as used in this Specification means physically discrete coherent units suitable for medical administration each containing a daily dose or a multiple (up to four times) or submultiple (down to a fortieth) of a daily dose of the compound of the invention in association with a carrier and/or enclosed within an envelope. Whether the medicament contains a daily dose or, for example, a half, a third or a quarter of a daily dose will depend on whether the medicament is to be administered once or, for example, twice, three times or four times a day respectively.

The diluents to be used in pharmaceutical compositions (e.g. granulates) adapted to be formed into tablets, dragees, capsules and pills include the following: (a) fillers and extenders, e.g. starch, sugars, mannitol, and silicic acid; (b) binding agents, e.g. carboxymethyl cellulose and other cellulose derivatives, alginates, gelatine and polyvinyl pyrrolidone; (c) moisturizing agents, e.g. glycerol; (d) disintegrating agents, e.g. agar-agar, calcium carbonate and sodium bicarbonate; (e) agents for retarding dissolution e.g. paraffin; (f) resorption accelerators, e.g. quaternary ammonium compounds; (g) surface active agents, e.g. cetyl alcohol, glycerol monostearate; (h) adsorptive carriers, e.g. kaolin and bentonite; (i) lubricants, e.g. talc, calcium and magnesium stearate and solid polyethyl glycols.

The tablets, dragees, capsules and pills formed from the pharmaceutical composition of the invention can have the customary coatings, envelopes and protective matrices, which may contain opacifiers. They can be so constituted that they release the active ingredient only or preferably in a particular part of the intestinal tract, possibly over a period of time. The coating, envelopes and protective matrices may be made, for example, of polymeric substances or waxes.

The active ingredient can also be made up in microencapsulated form together with one or several of the above-mentioned diluents.

Pharmaceutical compositions according to the invention can also contain colouring agents and preservatives as well as perfumes and flavouring additions (e.g. peppermint oil and eucalyptus oil) and sweetening agents (e.g. saccharin).

In addition to the nifedipine crystals of stated surface area, the pharmaceutical compositions and medicaments according to the invention can also contain other pharmaceutically active compounds.

Any diluent in the medicaments of the present invention may be any of those mentioned above in relation to the pharmaceutical compositions of the present invention.

The discrete coherent portions constituting the medicament according to the invention will generally be adapted by virtue of their shape or packaging for medical administration and may be, for example, any of the following: tablets (including lozenges and granulates), pills, dragees, capsules, sachets and multi-phase preparations, such as two-layer tablets. Some of these forms may be made up for delayed release of the active ingredient. Some, such as capsules, include a protective envelope which renders the portions of the medicament physically discrete and coherent.

Those solid medicaments and pharmaceutical compositions which contain nifedipine crystals with a specific surface area of 1 to 4 $m^2/g$ are particularly advantageous.

The nifedipine crystals which have a specific surface area of 0.5 to 6 $m^2/g$ and are used according to the invention are prepared by grinding the crystal mixtures obtained from the synthesis of nifedipine. Grinding can be effected, for example, with pin disc mills or hammer mills. Nifedipine with the desired surface area can be obtained by varying the speed of the mill, the amount of product fed in and/or the grinding period.

If a product with a relatively high specific surface area (for example 5 $m^2/g$) is desired, it is advantageous to carry out grinding with air jet mills. Crystals with a lower specific surface area (for example 0.5 $m^2/g$) are advantageously to be prepared by sieving in very fine sieves, preferably with mesh widths of 0.1 to 0.2 mm. In all cases, it is also possible to obtain a product with the desired specific surface area by mixing nifedipine crystals of different specific surface areas.

Accordingly the present invention also provides a process for the production of pharmaceutic compositions of the present invention in which nifedipine crystals obtained from the synthesis are converted in a crystal mixture with a specific surface area of 0.5 to 6 $m^2/g$ by grinding or sieving and the solid pharmaceutical compositions are formulated from these nifedipine crystals using one or more solid auxiliaries and/or excipients.

The specific surface are is measured by the gas adsorption method (BET method; see S. Brunauer: The adsorption of Gases and Vapours, Princeton (1945)).

Surprisingly, the solid formulations according to the invention have an unexpectedly high bio-availability. In the publication by I. Sugimoto et al, Drug Development and Industrial Pharmacy, 6(2), 137-160 (1980), it is particularly emphasised (see page 139) that, when administered orally, crystalline nifedipine is poorly absorbed and has only a very low bio-availability. It could thus not be expected that, after oral administration of the formulation according to the invention, which contains crystalline nifedipine, the plasma concentration rises rapidly and remains at a high value for many hours. In cases in which nifedipine must be taken over relatively long periods, it is sufficient, on the basis of this very high period of action, to administer 1 or 2 tablets daily. Another considerable advantage is that very small tablets with a high content of active compound can be prepared, since solubilising agents, surface-active substances and and additional auxiliaries can largely be dispensed with.

The smallness of the tablets and the surprisingly long period of action of the formulation according to the invention enable nifedipine to be used for the treatment of coronary illnesses over relatively long periods, and also prophylactically, and furthermore, this formulation presents the possibility of employing the hypotensive action of nifedipine for the treatment of hypertonia. The long-lasting blood level of the active compound which is obtainable by the formulation according to the invention represents an extension of the possibilities for using nifedipine in practice, and at the same time mean relief for the patients.

From the knowledge of the state of the art, from which it can be seen that the experts have for years been concerned with finding useful formulation forms for the active compound nifedipine, which is difficult to formulate, it is to be described as exceptionally surprising that a very simple and effective principle for galenical processing has been found by choosing a quite definite specific surface area of the active compound.

The solid formulation forms according to the invention represent relief for the patient during administration, and at the same time increase the reliability of the patient's treatment.

To demonstrate the advantageous action of the medicament formulations according to the invention, the plasma concentration of each of 8 persons was determined for several hours after the administration. The values can be seen from the following table:

TABLE

| | Time (hours) | | | | | | | |
|---|---|---|---|---|---|---|---|---|
| | 1 | 2 | 3 | 4 | 6 | 8 | 10 | 25.5 |
| Plasma concentration, µg/l after peroral administration of the tablets from Example 1 (20 mg) | 105.8 | 86.1 | 65.3 | 63.9 | 43.1 | 46.7 | 11.8 | 10.8 |
| Plasma concentration, µg/l after peroral administration of the tablets from Example 2 (20 mg) | 52.1 | 66.3 | 60.4 | 51.3 | 32.4 | 25 | 18.8 | 11.4 |

The following Examples illustrate processes for the production of solid medicament formulations according to the invention.

EXAMPLE 1

200 g of nifedipine crystals with a specific surface are of 4 $m^2/g$ were mixed with 348 g of microcrystalline cellulose, 100 g of lactose, 10 g of "Tween" 80, (Trade Mark), 70 g of starch and 2 g of magnesium stearate. A paste was prepared from a further 70 g of starch with water and, in the customary manner, the paste was granulated with the abovementioned mixture and the mixture was dried and then pressed to tablets which individually weighed 80 mg. These tables were then labelled; they had a diameter of 6 mm.

A suspension of 18 g of hydroxypropylmethylcellulose, 6 g of polyethylene glycol, 5.4 g of titanium dioxide, 0.6 g of iron oxide and 370 g of water or ethanol was used to lacquer 800 g of tablets.

EXAMPLE 2

200 g of nifedipine crystals with a specific surface area of 1 $m^2/g$ were pressed to 80 mg tablets with a diameter of 6 mm analogously to Example 1.

EXAMPLE 3

200 g of nifedipine with a specific surface area of 1.2 $m^2/g$ were mixed with 800 g of lactose, 960 g of starch and 40 g of magnesium stearate. 100 mg portions of the mixture were filled into size 3 hard gelatin capsules. Each capsule then contained 10 mg of nifedipine. Capsules containing various dosages, for example between 5 mg and 40 mg of active compound per capsule, could be prepared by varying the capsule size and the weight of contents.

EXAMPLE 4

Two-layer tables were prepared. One layer consisted of 7.5 mg of nifedipine with a specific surface area of 6 $m^2/g$, 7.5 mg of lactose, 30 mg of starch, 3 mg of polyvinylpyrrolidone and 2 mg of magnesium stearate (100 mg in total), and the second layer had the same composition, but the nifedipine had a specific surface area of 0.6 $m^2/g$. The compressed two-layer tablets weighing a total of 200 mg could be provided with a breaking groove in order to provide an individual dosage for the patient.

What is claimed is:

1. A solid pharmaceutical composition comprising as the active ingredient an effective amount of nifedipine crystals with a specific surface area of 1.0 to 4 $m^2/g$, in admixture with a solid diluent, to result in a sustained release of nifedipine.

2. A solid medicament in dosage unit form comprising an effective amount of nifedipine crystals with a specific surface area of 1.0 to 4 $m^2/g$, in admixture with a solid diluent, to result in a sustained release of nifedipine.

3. A medicament in the form of tablets, pills, dragees, capsules, suppositories, sachets or two-layer tablets comprising an effective amount of nifedipine crystals with a specific surface area of 1.0 to 4 $m^2/g$, in admixture with a solid diluent, to result in a sustained release of nifedipine.

4. In a method for treating hypertension by administering an effective amount therefor of nifedipine crystals to a patient, the improvement comprising employing nifedipine crystals having a specific surface area of 1.0 to 4 $m^2/g$, in admixture with a solid diluent, to result in a sustained release of nifedipine.

5. A solid pharmaceutical composition comprising as the active ingredient an effective amount of nifedipine crystals with a specific surface area of about 1.2 to 3.6 $m^2/g$, in admixture with a solid diluent, to result in a sustained release of nifedipine.

6. A solid medicament in dosage unit form comprising an effective amount of nifedipine crystals with a specific surface area of about 1.2 to 3.6 $m^2/g$, in admixture with a solid diluent, to result in a sustained release of nifedipine.

7. A medicament in the form of tablets, pills, dragees, capsules, suppositories, sachets or two-layer tablets comprising an effective amount of nifedipine crystals with a specific surface are of about 1.2 to 3.6 $m^2/g$, in admixture with a solid diluent, to result in sustained release of nifedipine.

8. In a method for treating hypertension by administering an effective amount therefor of nifedipine crystals to a patient, the improvement comprising employing nifedipine crystals having a specific surface area of about 1.2 to 3.6 $m^2/g$, in admixture with a solid diluent, to result in a sustained release of nifedipine.

9. A solid pharmaceutical composition comprising as the active ingredient an effective amount of nifedipine crystals with a specific surface area of 1.3 to 3.1 $m^2/g$, in admixture with a solid diluent, to result in a sustained release of nifedipine.

10. A solid medicament in dosage unit form comprising an effective amount of nifedipine crystals with a specific surface area of 1.3 to 3.1 $m^2/g$, in admixture with a solid diluent, to result in a sustained release of nifedipine.

11. A medicament in the form of tablets, pills, dragees, capsules, suppositories, sachets or two-layer tablets comprising an effective amount of nifedipine crystals with a specific surface area of 1.3 to 3.1 $m^2$, in admixture with a solid diluent, to result in a sustained release of nifedipine.

12. In a method for treating hypertension by administering an effective amount therefor of nifedipine crystals to a patient, the improvement comprising employing nifedipine crystals having a specific surface area of 1.3 to 3.1 $m^2/g$, in admixture with a solid diluent, to result in a sustained release of nifedipine.

* * * * *

UNITED STATES PATENT AND TRADEMARK OFFICE
CERTIFICATE OF CORRECTION

PATENT NO. : 5,264,446
DATED : November 23, 1993
INVENTOR(S) : Hegasy, et. al.

It is certified that error appears in the above-indentified patent and that said Letters Patent is hereby corrected as shown below:

Title page, item [63] Related U.S. Application Data, line 1, delete-- "576,103" and substitute -- 576,104--.

Column 6, line 17, delete "are" and substitute --area--.

line 18, after "in" insert -- a --.

Signed and Sealed this

Seventeenth Day of December, 1996

Attest:

BRUCE LEHMAN

*Attesting Officer*      *Commissioner of Patents and Trademarks*